United States Patent [19]

Eckenhoff et al.

[11] Patent Number: 4,678,467
[45] Date of Patent: Jul. 7, 1987

[54] DISPENSER COMPRISING CAPSULE WITH VOLUME DISPLACING MEMBER

[75] Inventors: James B. Eckenhoff; Felix Theeuwes, both of Los Altos; Joseph C. Deters, Mountain View, all of Calif.

[73] Assignee: ALZA Corporation, Palo Alto, Calif.

[21] Appl. No.: 829,351

[22] Filed: Feb. 13, 1986

Related U.S. Application Data

[62] Division of Ser. No. 591,824, Mar. 21, 1984, abandoned.

[51] Int. Cl.[4] ................................................ A61K 9/22
[52] U.S. Cl. ................................... 604/892; 604/893
[58] Field of Search ................................. 604/890–894

[56] References Cited

U.S. PATENT DOCUMENTS

| | | | |
|---|---|---|---|
| 3,845,770 | 11/1974 | Theeuwes et al. | 128/260 |
| 3,916,899 | 11/1975 | Theeuwes et al. | 128/260 |
| 4,014,334 | 3/1977 | Theeuwes et al. | 604/893 |
| 4,160,452 | 7/1979 | Theeuwes | 604/893 |
| 4,200,098 | 4/1980 | Ayer et al. | 128/260 |
| 4,285,987 | 8/1981 | Ayer et al. | 427/3 |
| 4,327,725 | 5/1982 | Cortese et al. | 604/893 |

*Primary Examiner*—C. Fred Rosenbaum
*Assistant Examiner*—Jerome R. Smith, Jr.
*Attorney, Agent, or Firm*—Paul L. Sabatine; Edward L. Mandell; Steven F. Stone

[57] ABSTRACT

A dispenser is disclosed for delivering a beneficial agent to an environment of use. The dispenser comprises a semipermeable wall surrounding a compartment containing a heat responsive composition, and an expandable composition. A passageway in the wall connects the compartment with the exterior of the dispenser.

2 Claims, 10 Drawing Figures

DISPENSER COMPRISING CAPSULE WITH VOLUME DISPLACING MEMBER

CROSS-REFERENCE TO RELATED APPLICATION

This application is a division of U.S. Ser. No. 06/591,824 filed on Mar. 21, 1984 now abandoned.

FIELD OF THE INVENTION

This invention pertains to both a novel and useful dispenser. More particularly, the invention relates to a dispenser comprising a semipermeable wall that surrounds in at least a part (a) or (b) a thermo-responsive beneficial agent formulation and an expandable driving member. The members comprising the dispenser perform in unison for delivering the beneficial agent at a controlled rate to an environment of use over time.

BACKGROUND OF THE INVENTION

Dispensers for delivering a beneficial agent to an environment of use are known to the dispensing art. For example, U.S. Pat. No. 3,760,984 issued to patentee Theeuwes discloses a dispenser consisting of a heat shrinkable container carrying on its outer surface an osmotic solute and a distant layer of a polymer permeable to fluid. The dispenser has a plug for filling the container. The dispenser is powered by fluid being imbibed into the dispenser, wherein it dissolves the solute, thereby forming a solution that exerts pressure against the shrinkable container, causing it to shrink and deliver agent from the dispenser. In U.S. Pat. No. 3,865,108 patentee Hartop discloses a dispenser consisting of an inner collapsible tube containing a medicament disposed in a base member formed of a swellable material. The dispenser delivers the medicament by the base and parts absorbing fluid from the environment, thereby expanding and squeezing the collapsible tube causing the medicine to be expelled from the tube. In U.S. Pat. No. 3,971,376 patentee Wichterle discloses a dispenser consisting of a capsule having unitary walls formed of a cross-linked gel that is swellable in fluids. A textile fabric is imbedded in the material for imparting strength and minimizing problems due to poor mechanical properties associated with the material that show themselves during fluid uptake used to power the dispenser. In U.S. Pat. No. 3,987,790, patentees Eckenhoff, et al., disclose an improvement in an osmotic dispenser consisting of a conduit for filling a bag in the dispenser. The dispenser is powered by an osmotically effective solute imbibing fluid into the dispenser, which imbibed fluid generates hydraulic pressure that is applied against the bag, causing it to squeeze inwardly forcing agent from the dispenser. In U.S. Pat. No. 3,995,631, patentees Higuchi, et al, disclose a bag bearing on its outer surface a layer of an osmotic solute, and a distant wall formed of a material having part controlled permeability to fluid. In operation, a solution is formed of the solute, which solution squeezes the bag thereby causing delivery of the agent from the bag. In U.S. Pat. No. 4,320,758 patentees Eckenhoff, et al., disclose a dispenser consisting of a flexible bag, a sleeve made of a dispersion of an osmotically effective solute in a soluble polymer, and an outer wall permeable to fluid. The dispenser delivers drug by the sleeve imbibing water into the space between the outer wall and the bag, thereby exerting hydraulic pressure on the bag, which pressure causes the bag to be squeezed and delivers drug from the bag. U.S. Pat. No. 4,350,271 discloses a fluid dispenser that operates by absorbing water into a composition that expands against a lipophilic fluid that is dispensed via an outlet.

While the above dispensers are useful for delivering numerous agents to the environment of use, and while the dispensers represent a commercial advancement in the dispensing art, it will be appreciated by those skilled in the art that there are instances where a dispenser made with an inventively novel improvement would also enjoy wide commercial use and application in the dispensing art. For example, if a dispenser is provided having an initial internal capsule arrangement that makes the manufacture of the dispenser easier and more efficient at a reduced cost, and if the dispenser is made without a flexible bag and without a fabric member, thereby providing an improvement in the dispenser by reducing the number of steps and parts needed to make the dispenser, such a dispenser would have immediate acceptance, and it would also represent a major advancement in the art. Likewise, if a dispenser is provided that overcomes the prior art dispenser limitation of delivering agents only in solution or suspension forms, by the dispenser now delivering agents that are soluble or insoluble in fluid, semi-solid or like forms, such a dispenser would enjoy instant appreciation and also represent a valuable contribution in the fields of science, medicine and commerce.

OBJECTS OF THE INVENTION

Accordingly, it is an immediate object of this invention to provide a dispenser for delivering beneficial agents in all useful forms to environments of use, with a novel dispenser that represents an improvement in the dispenser art.

Another object of the invention is to provide a dispenser that is self-contained, self-starting, and self-powered in fluid environments, is easy to manufacture, and can be used for dispensing beneficial agents to animals, including humans, and to other biological and non-biological environments of use.

Another object of the invention is to provide a dispenser that can house a thermo-responsive, hydrophobic composition comprising insoluble to soluble drugs, and which thermo-responsive composition in response to the temperature of a biological environment changes its form and becomes fluid, semi-solid, or the like for enhanced delivery from the dispenser.

Yet another object of the invention is to provide a dispenser having an initial, internal capsule arrangement that makes it easier to manufacture the dispenser at a lesser cost, thereby increasing the practicality of the dispenser.

Yet another object of the invention is to provide a dispenser comprising a lumen containing a temperature-sensitive composition, an expandable member in parallel arrangement with the temperature-sensitive composition, an inner capsule containing the composition and the member in the lumen of the capsule, an outer semipermeable wall surrounding in at least a part, the capsule, and a dispensing passageway, and which dispenser delivers the composition by the combined physical-chemical operations of the composition melting and becoming fluid to semi-solid or the like, with the composition maintaining an immiscible boundary at the expanding member interface, and the expanding member swelling into the space occupied by the composition to displace an equivalent amount of composition from the dispenser.

Yet another object of the invention is to provide a dispenser that is empty until filled with a solid composition that liquifies at elevated temperatures, and when filled can administer the composition that liquifies as a complete pharmaceutical dosage regimen for a period of time, the use of which requires intervention only for the initiation and the termination of the regimen.

Yet another object of the invention is to provide a dispenser that can deliver beneficial drugs contained in a thermo-responsive, lipophilic pharmaceutically acceptable carrier that melts in the presence of thermal energy absorbed from a biological environment of use into the dispensable composition that is innocuous, thereby substantially avoiding mammalian tissue irritation and interaction with mammalian protein tissue.

Still another object of the invention is to provide an osmotic dispenser containing a eutectic composition formed of at least two components and at least one drug, which eutectic composition has a melting point approximately the same as the temperature of a warm blooded animal, and is dispensed from the dispenser to the animal at said temperature.

Yet another object of the invention is to provide a dispenser comprising an inner placed capsule housing a thermo-responsive hydrophilic composition comprising insoluble to soluble drugs, and which thermo-responsive composition in response to energy input present in a biological environment of use, changes its form and becomes dispensable for operative delivery from the dispenser.

Yet another object of the invention is to provide a dispenser comprising an inner capsule containing a thermoplastic composition and an expandable component, and which composition includes a beneficial agent that is chemically unstable in an aqueous environment and can be housed in the dispenser in a nonaqueous dispensing carrier, which agent is shielded in the nonaqueous carrier during delivery from the dispenser.

Yet another object of the invention is to provide a dispenser comprising a semipermeable wall surrounding in at least a part a compartment containing a thermo-responsive composition containing an active agent, and means for urging the composition through a passageway that connects the compartment with the exterior of the dispenser.

Other objects, features and advantages of the invention will be more apparent to those skilled in the dispensing art from the following detailed description of the specification, taken in conjunction with the drawings and the accompanying claims.

BRIEF DESCRIPTION OF THE DRAWINGS

In the drawings, which are not drawn to scale, but are set forth to illustrate various embodiments of the invention, the drawing figures are as follows.

In the drawings and the specification, like parts in related figures are identified by like parts. The terms appearing earlier in the specification and in the description of the drawings, as well as embodiments thereof, are further detailed elsewhere in the disclosure.

DETAILED DESCRIPTION OF THE DRAWINGS

Figure 1:
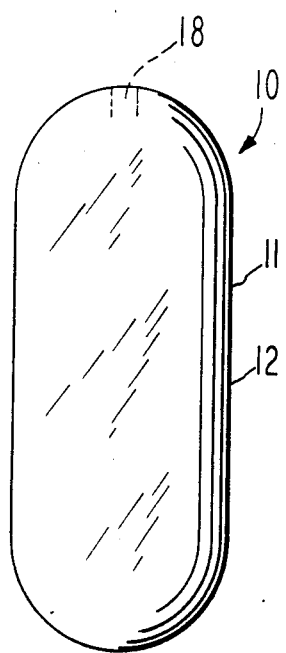
FIG. 1 is a view of a dispenser designed with a one-piece configuration and manufactured for orally administering a beneficial drug to a warm-blooded animal.

Turning now to the drawing figures in detail, which are examples of new and useful dispensers for dispensing a beneficial agent, and which examples are not to be construed as limiting, one example of a dispenser is depicted in FIG. 1 identified by the numeral 10. In FIG. 1 dispenser 10 comprises a body 11 formed of a wall 12 that surrounds and defines an internal lumen or space, not seen in FIG. 1, and a passageway 18 indicated by dashes.

Figure 2:
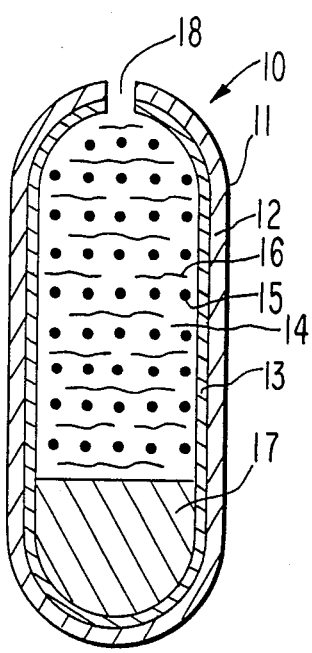
FIG. 2 is an opened view of the dispenser of FIG. 1 through the vertical length of the dispenser, for illustrating the internal compartment containing a thermodynamic thermo-responsive member and the expandable member forming the dispenser and manufactured as an integral system.

FIG. 2 is an opened view of dispenser 10 of FIG. 1. Dispenser 10 of FIG. 2 comprises body 11 and wall 12. Wall 12 is formed of a semipermeable polymeric wall forming composition that is substantially permeable to the passage of external fluid, and it is substantially impermeable to the passage of beneficial agent and other ingredients contained in dispenser 10. Wall 12 is nontoxic and it maintains its physical and chemical integrity, that is it doesn't erode during the dispensing period. Dispenser 10 is made in its final manufacture comprising a single unit capsule 13. That is capsule 13 cannot be easily separated into parts. Capsule 13 and subsequent use of the term capsule implies either hard or soft in structure as embodied herein. Further, in FIG. 2, capsule 13 surrounds an internal lumen or space 14. Lumen 14 contains a beneficial agent 15, identified by dots, a thermo-responsive heat sensitive composition 16, identified by wavy lines, and a driving member 17 that is in layered contact with the surface of composition 16. Driving member 17 in a preferred embodiment is an expandable member 17 has a shape that corresponds to the internal shape of capsule wall 13 and compartment 14. Expandable member 17 in a layer-form is made from a hydrogel composition, that is noncross-linked or optionally cross-linked, and it possesses osmotic properties, such as the ability to imbibe an exterior fluid through semipermeable wall 12 and exhibit an osmotic pressure gradient across semipermeable wall 12 against a fluid outside dispenser 10. In another embodiment driving member 17 can be a solid osmotically effective solute that imbibes fluid through semipermeable wall 12. Dispenser 10 is made with a passageway 18 in semipermeable wall 12 and through capsule 13. Passageway 18 communicates with compartment 14 and the exterior of dispenser 10 for delivering beneficial agent 15 from dispenser 10.

In FIG. 2, thermo-responsive, heat-sensitive composition 16, is a delivery means and a transporting carrier for beneficial agent 15. The beneficial agent 15 is housed in compartment 14 that can be delivered by dispenser 10, includes agents that are from insoluble to very soluble in both aqueous fluids and in lipophilic medium.

The thermo-responsive composition 16, containing agent 15 homogeneously or heterogeneously dispersed or dissolved therein, is formed in a presently preferred embodiment of an anhydrous, heat sensitive, hydrophilic or hydrophobic material that exhibits solid-like properties at room temperature of 21° C., and within a few centrigrade degrees thereof, and exhibits a melting point that approximates mammalian body temperatures of 37° C., and with a few centrigrade degrees thereof. The present invention uses the phrases "melting point", "softening point", or "liquifies" to indicate the temperature at which the thermo-responsive composition melts, undergoes dissolution, or dissolves to form a dispensable carrier so it can be used for dispensing agent 15 from dispenser 10.

Figure 3:
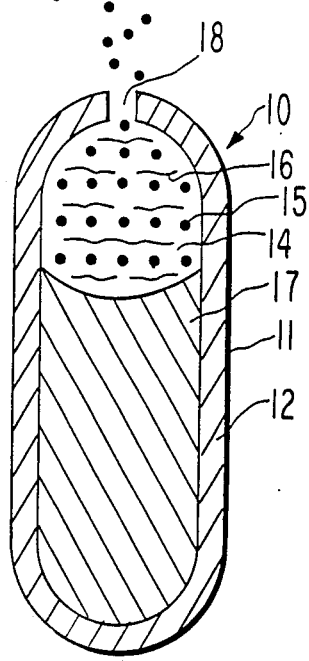
FIG. 3 is an opened view of the dispenser of FIG. 1 and FIG. 2 with FIG. 3 depicting the dispenser comprising a semipermeable wall surrounding a compartment charged with the temperature sensitive composition and a driving member in operation and dispensing a beneficial agent.

FIG. 3 depicts dispenser 10 of FIGS. 1 and 2 in operation delivering beneficial agent 15 to a fluid environment of use. In operation, when in the environment of use having a temperature of 37° C. within a few degrees, dispenser 10 delivers agent 15 by a combination of thermodynamic and kinetic activities. This is, in operation heat-sensitive composition 16 melts and forms a fluidic, a semi-solid, or a like deliverable phase, for delivering agent 15 through passageway 18. As composition 16 melts, fluid is imbibed through semipermeable wall 12 by hydrophilic member 17 in a tendency towards osmotic equilibrium, to continuously swell, or expand or to fill, and increase the volume of member 17 and simultaneously member 17 expands in compartment 14 while substantially maintaining an intact immiscible boundary at the interface. As external fluid is imbibed through semipermeable wall 12 into dispenser 10, capsule wall 13 formed of a fluid dissolvable material slowly dissolves and lubricates the inside of the dispenser which assists in the undisturbed expansion of member 17 and the resultant continuous release of composition 16. Concomitantly, as volume increasing member 17 increases its volume, it applies pressure against composition 16 urging composition to decrease its volume. The simultaneous occurrences of the expansion of member 17, the contraction of compartment 14, and the melting of composition 16 causes composition 16 containing agent 15 to be delivered through passageway 18 to the exterior of dispenser 10. FIGS. 2 and 3 considered together illustrate dispenser 10 in operation delivering agent 15. FIG. 2 depicts dispenser 10 at the beginning of an agent delivery period, and FIG. 3 depicts dispenser 10 nearing the end of an agent delivery period. The melting of composition 16, the immiscibility of composition 16 with member 17 and the swelling, filling, and expansion of means 17, with its accompanying increase in volume as seen in FIG. 3, along with the simultaneous corresponding reduction in volume of compartment 14 as seen in FIG. 3, assures the delivery of agent 15 at a controlled rate and continuously over time.

Figure 4:
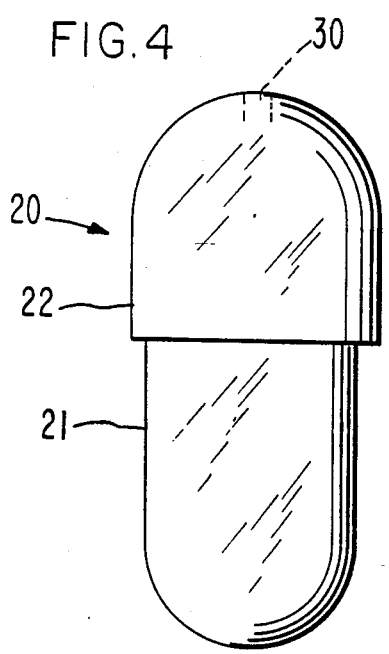
FIG. 4 is a view of a dispenser comprising two telescoping parts and manufactured for delivering a beneficial agent over time.

FIG. 4 illustrates a dispenser 20 comprising two parts, a body member 21 and a cap member 22 manufactured into a unit dispenser. Dispenser 20 is made conveniently in two parts with one part 22 slipping over and capping the other part 21. Parts 21 and 22 completely surround and capsulate an internal lumen, not seen in FIG. 4. Dispenser 20 also includes a passageway 30, indicated by dashes.

Figure 5:
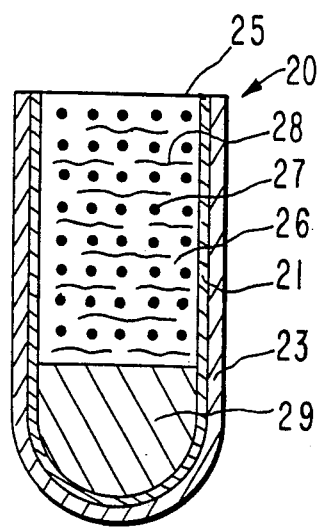
FIG. 5 is an opened-sectioned view of FIG. 4 comprising the body portion of the dispenser free of the telescopically engaging cap portion of the dispenser.
Figure 6:
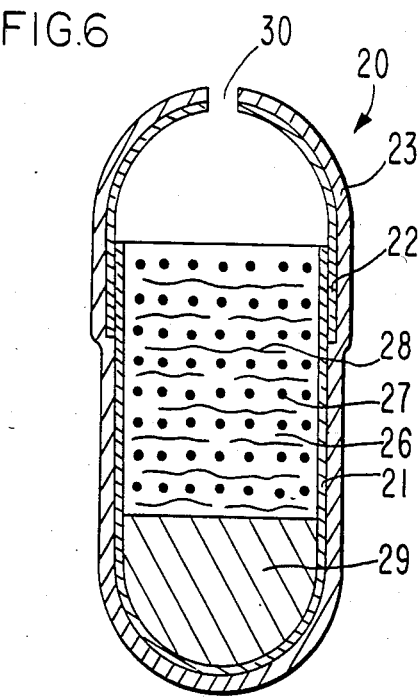
FIG. 6 is an opened-section view of FIG. 4 depicting the body portion telescopically capped by an engaging cap portion, with the lumen of the dispenser charged with a temperature-sensitive agent containing composition and an expandable, driving member.

FIG. 5 is an opened view of the uncapped dispenser of FIG. 4. In FIG. 5, dispenser 20 comprises a body member 21 consisting essentially a semipermeable wall 23 that surrounds in at least a part and intimately contacts internal body capsule 21, except at mouth 25 of capsule 21. The capsule used for forming the dispenser comprises two parts, ingredient receiving capsule body member 21 and a cap member 22 as seen in FIG. 6. Capsule member 21 surrounds space 26 containing a beneficial agent 27, identified by dots, a thermo-responsive heat sensitive composition 28, identified by wavy lines, and an expandable, swellable piston-like driving member 29 that is in parallel arrangement with the interfaced contacting surface of composition 29. The material comprising the parts of FIG. 5 are formed of materials discussed for FIGS. 1–3, and they are further discussed later in the specification.

Figure 7:
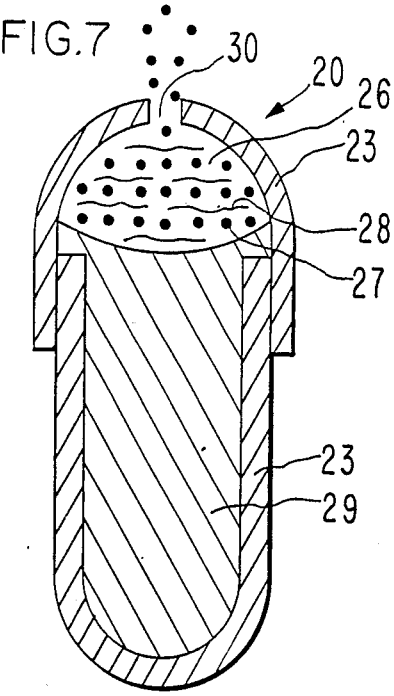
FIG. 7 is an opened-sectioned view of the dispenser of FIG. 4 and FIG. 6 illustrating in FIG. 7 the dispenser comprising a semipermeable wall surrounding a compartment and in operation delivering a beneficial agent over time.

FIG. 6 is an opened view of FIGS. 4 and 5. FIG. 6 depicts dispenser 20 capped with 22. In FIG. 6, cap 22 is fitted over capsule body 21 after the larger body 21 is filled with all the preselected appropriate drugs, heat-sensitive compositions and drivng members. In FIG. 6, after cap 22 is fitted over body 21, a semipermeable wall 23 is applied over the exterior surface of body member 21 and cap 22. In another manufacture, capsule body 21 is filled with the respective ingredients and a semipermeable wall applied except for the mouth, and then it is capped with cap 22. Then cap 22 telescoped over body 21 is coated with a semipermeable wall 23. A passageway 30, in either manufacture is drilled through the semipermeable wall 23 and capsule wall 22 for dispensing agent 27 from dispenser 20. FIG. 7 depicts device 20 in operation. In FIG. 7, the dispenser is depicted comprising only semipermeable wall 23 nearing the end of the delivery period. Dispenser 20 operates in the manner described above for dispenser 10.

Figure 8:
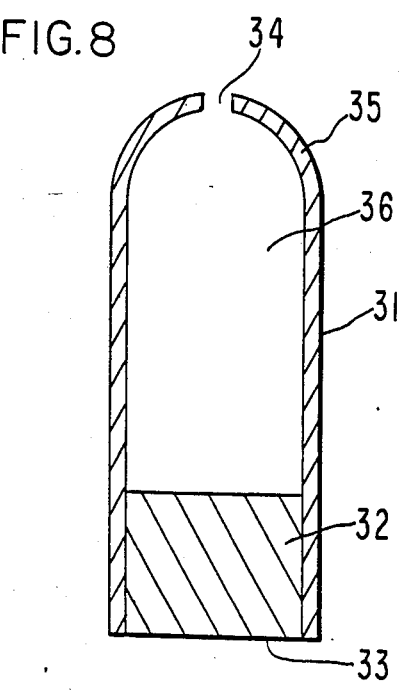
FIG. 8 is an opened view of the body portion of a capsule comprising an expandable, swellable plug in the mouth of the capsule.
Figure 9:
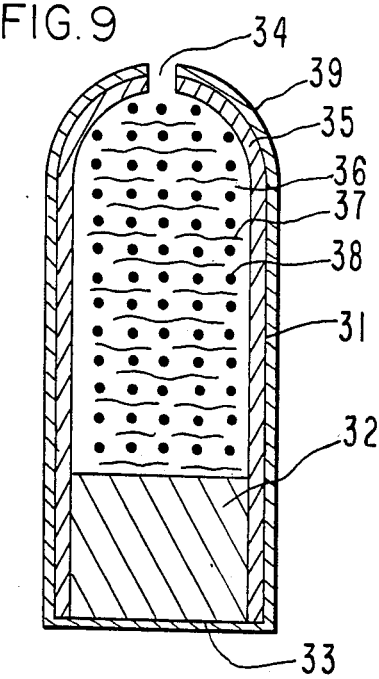
FIG. 9 is an opened view as seen in FIG. 8 of the body portion of a capsule comprising an expandable, swellable plug in parallel arrangement with a thermosensitive agent containing composition; and, FIG. 10 is a graph depicting the release pattern of a drug formulation from a dispenser over a prolonged period of time.

FIG. 8 depicts another embodiment provided for enhancing the manufacture and the usefulness of the dispenser. In FIG. 8, there is illustrated a body such as the body portion 31 in a preferred embodiment, a capsule, having an expandable plug 32 inserted into mouth 33 of body portion 31. The body member can be made of a semipermeable material or of a hydrophilic material. A passageway 34 is drilled through wall 35 of body portion 31 distant from expandable plug 32 for inserting a filling instrument into body portion 31 for filling space 36. FIG. 9 depicts space 36 filled with a thermo-sensitive composition 37 containing beneficial agent 38. After the space is filled, the body or the capsule is coated and surrounded with a semipermeable wall 39. The semipermeable wall provides in either embodiment a means for imbibing fluid into expandable member 32 and it closes mouth 33, thereby assuring that expansion of plug 32 will be unidirected in space 36 towards passageway 34. In this manufacture a passageway 34 is drilled through the semipermeable wall in linear arrangement with the passageway in the capsule wall for delivering agent 38 from the capsule. In another manufacture a semipermeable wall 39 is coated around an empty capsule member having a plug in its mouth, a passageway is drilled through the semipermeable wall and the capsule wall, and then the capsule space is filled with a thermo-sensitive composition containing beneficial agent.

While FIGS. 1 through 9 illustrate various dispensers that can be made according to the invention, it is to be understood those dispensers are not to be construed as limiting the invention, as the dispenser can take a wide variety of shapes, sizes and forms for delivering beneficial agents to the environment of use. For example, the dispenser can be made for oral use and the dispenser can be adapted for use as a buccal, implant, artificial gland, cervical, intrauterine, ear, nose, dermal, vaginal, anorectal, ruminal, such as the reticulum of cattle, and subcutaneous dispenser. The dispenser also can be shaped, sized and structured and adapted for delivering an active agent in streams, aquariums, fields, factories, reservoirs, laboratory facilities, hot houses, transportation means, hospitals, naval and military means, veterinary clinics, nursing homes, farms, zoos, sickrooms, chemical reactors, and other environments of use.

DETAILED DESCRIPTION OF THE INVENTION

In accordance with the practice of this invention, it has now been surprisingly found that dispenser 10 and dispenser 20 can be made with a capsule that possess two distinct forms, classified for the purpose of this invention, as osmotic hard capsule and osmotic soft capsule. The osmotic hard capsule is composed of two parts, a cap and a body, which are fitted together after the larger body is filled with a preselected appropriate agent formulation. This is done by slipping or telescoping the cap section over the body section, thus completely surrounding and encapsulating the useful agent formulations. Hard capsules are made by dipping molds into a bath containing a solution of a capsule lamina-forming material to coat the mold with the material. Then, the molds are withdrawn, cooled, and dried in a current of air. The capsule is stripped from the mold and trimmed to yield a lamina member with an internal lumen. The engaging cap that telescopically caps the agent formulation receiving body is made in a similar manner. Then, the closed and filled osmotic capsule is capsuled with a semipermeable wall or lamina. The semipermeable wall can be applied to capsule parts either before or after the parts are joined into the final capsule. In another embodiment, the hard capsules can be made with each part having, matched locking rings near their opened end that permit joining and locking together the overlapping cap and body after filling with agent formulation. In this embodiment, a pair of matched locking rings are formed into the cap portion and the body portion, and these rings provide the locking means for securely holding together the capsule. The capsule can be manually filled with the agent formulation, or it can be machine filled with the agent formulation. In the final manufacture the hard capsule is capsuled with a semipermeable lamina permeable to the passage of fluid and substantially impermeable to the passage of useful agent as described hereafter.

The osmotic soft capsule as used by the present invention, preferably in its final form, comprises one piece. Generally, the osmotic soft capsule is of sealed construction encapsulating the useful agent formulation therein. The soft capsule is made by various processes including the plate process, the rotary die process, the reciprocating die process. and the continuous process. The plate process uses a set of molds. A warm sheet of a prepared capsule lamina-forming material is laid over the lower mold and the agent formulation poured on it. A second sheet of the lamina-forming material is placed over the agent formulation followed by the top mold. The mold set is placed under a press and a pressure applied, with or without heat to form a unit, soft capsule. The capsules are washed with a solvent for removing excess agent formulation from the exterior of the capsule, and the air-dried capsule is capsulated with a lamina of a semipermeable material.

The rotary die process uses two continuous films of capsule lamina-forming material that are brought into convergence between a pair of revolving dies and an injector wedge. The process fills and seals the capsule in dual and coincident operations. In this process, the sheets of capsule lamina-forming material are fed over guide rolls, and then down between the wedge injector and the die rolls. The agent formulation to be capsuled flows by gravity into a positive displacement pump. The pump meters the agent formulation through the wedge injector and into the sheets between the die rolls. The bottom of the wedge contains small orifices lined up with the die pockets of the die rolls. The capsule is about half-sealed when the pressure of pumped agent formulation forces the sheets into the die pockets, wherein the soft capsules are simultaneously filled, shaped, hermetically sealed and cut from the sheets of lamina-forming materials. The sealing of the soft capsule is achieved by mechanical pressure on the die rolls and by heating of the sheets of lamina-forming materials by the wedge. After manufacture, the agent formulation-filled capsules are dried in the presence of forced air, and a semipermeable lamina capsuled thereto, by processes described hereafter.

The reciprocating die process produces soft capsules by leading two films of capsule lamina-forming material between a set of vertical dies. The dies as they close, open and close, perform as a continuous vertical plate forming row after row of pockets across the film. The pockets are filled with agent formulation, and as the pockets move through the dies, they are sealed, shaped and cut from the moving film as capsules filled with agent formulation. A semipermeable lamina is coated thereon to yield the osmotic, soft capsule dispenser. The continuous process is a manufacturing system that also uses rotary dies with the added feature that the process can successfully fill active agent in dry powder form into a soft capsule, in addition to encapsulating liquids. The filled, soft capsule of the continuous process is encapsulated with a semipermeable polymeric material to yield the osmotic soft capsule.

The dispenser of this invention can be provided with a wall comprising a semipermeable material that does not adversely affect a host or animal, is permeable to the passage of an external aqueous type fluid, such as water and biological fluids, while remaining essentially impermeable to the passage of agents, including drugs, and maintains its integrity in the presence of a thermotropic thermo-responsive composition, that is it does not melt or erode in said presence. The selectively semipermeable materials forming the outer wall are substantially insoluble in fluids, they are nontoxic, and they are non-erodible.

Representative materials for forming the semipermeable wall include semipermeable homopolymers, semipermeable copolymers, and the like. In one embodiment typical materials include cellulose esters, cellulose monoesters, cellulose diesters, cellulose triesters, cellulose ethers, cellulose ester-ethers and mixtures thereof. These cellulosic polymers have a degree of substitution, D.S., on their anhydroglucose unit from greater than 0 up to 3 inclusive. By degree of substitution is meant the average number of hydroxyl groups originally present on the anhydroglucose unit that are replaced by a substituting group, or converted into another group. The anhydroglucose unit can be partially or completely substituted with groups such as acyl, alkanoyl, aroyl, alkyl, alkenyl, alkoxy, halogen, carboalkyl, alkylcarbamate, alkylcarbonate, alkylsulfonate, alkylsulfamate, and like semipermeable polymer forming groups.

The semipermeable materials typically include a member selected from the group consisting of cellulose acylate, cellulose diacylate, cellulose triacylate, cellulose acetate, cellulose diacetate, cellulose triacetate, mono-, di- and tri-cellulose alkanylates, mono-, di- and tri-alkenylates, mono-, di- and tri-aroylates, and the like. Exemplary polymers including cellulose acetate having a D.S. of 1.8 to 2.3 and an acetyl content of 32 to 39.9%; cellulose diacetate having a D.S. of 1 to 2 and an acetyl content of 21 to 35%; cellulose triacetate having a D.S of 2 to 3 and an acetyl content of 34 to 44.8%, and the like. More specific cellulosic polymers include cellulose propionate having a D.S. of 1.8 and a propionyl content of 38.5%; cellulose acetate propionate having an acetyl content of 1.5 to 7% and an acetyl content of 39 to 42%; cellulose acetate propionate having an acetyl content of 2.5 to 3%, an average propionyl content of 39.2 to 45% and a hydroxyl content of 2.8 to 5.4%; cellulose acetate butyrate having a D.S. of 1.8, an acetyl content of 13 to 15%, and a butyryl content of 34 to 39%; cellulose acetate butyrate having an acetyl content of 2 to 29.5%, a butyryl content of 17 to 53%, and a hydroxyl content of 0.5 to 4.7%; cellulose triacylates having a D.S. of 2.9 to 3 such as cellulose trivalerate, cellulose trilaurate, cellulose tripalmitate, cellulose trioctanoate, and cellulose tripropionate; cellulose diesters having a D.S. of 2.2 to 2.6 such as cellulose disuccinate, cellulose dipalmitate, cellulose dioctanoate, cellulose dicarpylate and the like; mixed cellulose esters such as cellulose acetate valerate, cellulose acetate succinate, cellulose propionate succinate, cellulose acetate octanoate, cellulose valerate palmitate, cellulose acetate heptonate, and the like. Semipermeable polymers are known in U.S. Pat. No. 4,077,407, and they can be made by procedures described in *Encyclopedia of Polymer Science and Technology*, Vol. 3, pages 325 to 354, 1964, published by Interscience Publishers, Inc., New York.

Additional semipermeable polymers include acetaldehyde dimethyl cellulose acetate; cellulose acetate ethylcarbamate; cellulose acetate methylcarbamate; cellulose dimethylaminoacetate; semi-permeable polyamides; semipermeable polyurethanes; semi-permeable polysulfanes; semipermeable sulfonated polystyrenes, cross-linked, selectively semipermeable polymers formed by the coprecipitation of a polyanion and a polycation as disclosed in U.S. Pat. Nos. 3,173,876; 3,276,586; 3,541,005; 3,541,006, and 3,546,142; selectively semipermeable silicon rubbers; semipermeable polymers as disclosed by Loeb and Sourirajan in U.S. Pat. No. 3,133,132; semipermeable polystyrene derivates; semipermeable poly(sodium styrenesulfonate); semipermeable poly(vinylbenzyltrimethyl) ammonium chloride; semipermeable polymer exhibiting a fluid permeability of $10^{-1}$ to $10^{-7}$ (cc.mil/cm$^2$ hr.atm) expressed as per atmosphere of hydrostatic or osmotic pressure difference across a semipermeable wall. The polymers are known to the art in U.S. Pat. Nos. 3,845,770; 3,916,899, and 4,160,020, and in *Handbook of Common Polymers*, by Scott, J. R. and Roff, W. J., 1971, published by CRC Press, Cleveland, Ohio.

The materials used for forming the swellable, expandable inner member or layer and the plug, are polymeric materials neat, and polymeric materials blended with osmotic agents that interact with water or a biological fluid, absorb the fluid and swell or expand to an equilibrium state. The polymer exhibits the ability to retain a significant fraction of imbibed fluid in the polymer molecular structure. The polymers in a preferred embodiment are gel polymers that can swell or expand to a very high degree, usually exhibiting a 2 to 50 fold volume increase. The swellable, hydrophilic polymers, also known a osmopolymers can be noncross-linked or lightly cross-linked. The cross-links can be covalent or ionic bonds with the polymer possessing the ability to swell in the presence of fluid, and when cross-linked it will not dissolve in the fluid. The polymer can be of plant, animal or synthetic origin. Polymeric materials useful for the present purpose include poly(hydroxyalkyl methacrylate) having a molecular weight of from 5,000 to 5,000,000; poly(vinylpyrrolidone) having a molecular weight of from 10,000 to 360,000; anionic and cationic hydrogels; poly(electrolyte) complexes; poly(vinyl alcohol) having a low acetate residual; a swellable mixture of agar and carboxymethyl cellulose; a swellable composition comprising methyl cellulose mixed with a sparingly cross-linked agar; a water-swellable copolymer produced by a dispersion of finely divided copolymer of maleic anhydride with styrene, ethylene, propylene, or isobutylene; water swellable polymer of N-vinyl lactams; and the like.

Other gelable, fluid imbibing and retaining polymers useful for forming the hydrophilic, expandable push member include pectin having a molecular weight ranging from 30,000 to 300,000; polysaccharides such as agar, acacia, karaya, tragacanth, algins and guar; Carbopol ® acidic carboxy polymer and its salt derivatives; polyacrylamides; water-swellable indene maleic anhydride polymers; Good-rite ® polyacrylic acid having a molecular weight of 80,000 to 200,000; Polyox ® polyethylene oxide polymers having a molecular weight of 100,000 5,000,000, and greater; starch graft copolymers; polyanions and polycations exchange polymers; starch-polyacrylonitrile copolymers. Aqua-Keep ® acrylate polymers with water absorbability of about 400 times its original weight; diesters of polyglucan; a mixture of cross-linked polyvinyl alcohol and poly(N-vinyl-2-pyrrolidone); zein available as prolamine; poly(ethylene glycol) having a molecular weight of 4,000 to 100,000; and the like. In a preferred embodiment, the expandable wall is formed from polymers and polymeric compositions that are thermoformable. Representative polymers possessing hydrophilic properties are known in U.S. Pat. Nos. 3,865,108; 4,002,173; 4,207,893; 4,327,725, and in *Handbook of Common Polymers*; by Scott and Roff, published by Cleveland Rubber Company, Cleveland, Ohio.

The osmotically effective compound that can be used neat or it can be blended homogeneously or heterogeneously with the swellable polymer, to form a push member, are the osmotically effective solutes that are soluble in fluid imbibed into the swellable polymer, and exhibit an osmotic pressure gradient across the semipermeable wall against an exterior fluid. Osmotically effective compounds are known also as osmagents. Osmotically effective osmagents useful for the present purpose include solid compounds selected from the group consisting of magnesium sulfate, magnesium chloride, sodium chloride, lithium chloride, potassium sulfate, sodium sulfate, mannitol, urea, sorbitol, inositol, sucrose, glucose, and the like. The osmotic pressure in atmospheres, ATM, of the osmagents suitable for the invention will be greater than zero ATM, generally from zero ATM up to 500 ATM, or higher.

The swellable, expandable polymer, in addition to providing a driving source for delivering a beneficial agent from the dispenser, further serves to function as a supporting matrix for an osmotically effective solute. The osmotic solute can be homogeneously or heterogeneously blended with the polymer to yield the desired expandable wall or expandable pocket. The composition in a presently preferred embodiment comprises (a) at least one polymer and at least one osmotic solute, or (b) at least one solid osmotic solute. Generally, a composition will comprise about 20% to 90% by weight of polymer and 80% to 10% by weight of osmotic solute, with a presently preferred composition comprising 35% to 75% by weight of polymer and 65% to 25% by weight of osmotic solute.

The term thermo-responsive as used for the purpose of this invention includes thermoplastic compositions capable of softening, or becoming dispensable in response to heat and hardening again when cooled. The term also includes thermotropic compositions capable of undergoing change in response to the application of energy in a gradient manner. These are temperature sensitive in their response to the application or withdrawl of energy. The term thermo-responsive as used for the purpose of this invention in a preferred embodiment denotes the physical-chemical property of a composition agent carrier to exhibit solid, or solid-like properties at temperatures up to 33° C., and become fluid, semisolid, or viscous when disturbed by heat at temperatures from 32° C., usually in the range of 32° to 40° C. The thermo-responsive carrier is heat-sensitive and it has the property of melting, dissolving, undergoing dissolution, softening, or liquifying and thereby forming a dispensible composition at the elevated temperatures, thereby making it possible for the dispenser to deliver the thermo-responsive carrier with the beneficial agent homogeneously or heterogeneously blended therein. The thermo-responsive carrier can be lipophilic, hydrophilic or hydrophobic. Another important property of the carrier is its ability to maintain the stability of the agent contained therein during storage and during delivery of the agent. Representative thermo-responsive compositions and their melting points are as follows: Cocoa butter 32°–34° C.; cocoa butter plus 2% beeswax 35°–37° C.; propylene glycol monostearate and distearate 32°–35° C.; hydrogenated oils such as hydrogenated vegetable oil 36°–37.5° C.; 80% hydrogenated vegetable oil and 20% sorbitan monopalmitate 39–39.5%; 80% hydrogenated vegetable oil and 20% polysorbate 60, 36°–37° C.; 77.5% hydrogenated vegetable oil, 20% sorbitan trioleate and 2.5% beeswax 35°–36° C.; 72.5% hydrogenated vegetable oil, 20% sorbitan trioleate, 2.5% beeswax and 5.0% distilled water, 37°–38° C.; mono-, di-, and triglycerides of acids having from 8-22 carbon atoms including saturated and unsaturated acids such as palmitic, stearic, oleic, linoleic, linolenic and archidonic; triglycerides of saturated fatty acids with mono- and diglycerides 34°–35.5° C.; propylene glycol mono- and distearates 33°–34° C.; partially hydrogenated cottonseed oil 35°–39° C.; a block polymer of polyoxy-alkylene and propylene glycol; block polymers comprising 1,2-butylene oxide to which is added ethylene oxide; block copolymers of propylene oxide and ethylene oxide; hardened fatty alcohols and fats 33°–36° C.; hexadienol and hydrous lanolin triethanolamine glyceryl monostearate 38° C.; eutectic mixtures of mono-, di-, and triglycerides 35°–39° C.; Witepsol ® #15, triglyceride of saturated vegetable fatty acid with monoglycerides 33.5°–35.5° C.; Witepsol ® H32 free of hydroxyl groups 31°–33° C.; Witepsol ® W25 having a saponification value of 225-240 and a melting point of 33.5°–35.5° C.; Witepsol ® E75 having a saponification value of 220-230 and a melting point of 37°–39° C.; a polyalkylene glycol such as polyethylene glycol 1000, a linear polymer of ethylene oxide, 38°–41° C.; polyethylene glycol 1500, melting at 38°–41° C.; polyethylene glycol monostearate 39°–42.5° C.; 33% polyethylene glycol 1500, 47% polyethylene glycol 6000 and 20% distilled water 39°–41° C.; 30% polyethylene glycol 1500, 40% polyethylene glycol 4000 and 30% polyethylene glycol 400, 33°–38° C.; mixture of mono-, di-, and triglycerides of saturated fatty acids having 11 to 17 carbon atoms, 33°–35° C., and the like. The thermo-responsive composition is a means for storing a beneficial agent in a solid composition at a temperature of 20°–33° C., maintaining an immiscible boundary at the swelling composition interface, and for dispensing the agent in a flowable composition at a temperature greater than 33° C., and preferably in the range of 33°–40° C. The thermo-responsive composition on being dispensed into a biological environment are easily excreted, metabolized, assimilated, or the like, for effective use of the beneficial agent.

The materials used for forming the capsule are the commercially available materials including gelatin, gelatin having a viscosity of 15 to 30 millipoises and a bloom strength up to 150 grams; gelatin having a bloom value of 160 to 250; a composition comprising gelatin, glycerine water and titanium dioxide; a composition comprising gelatin, erythrosin, iron oxide and titanium dioxide; a composition comprising gelatin, glycerine, sorbitol, potassium sorbate and titanium dioxide; a composition comprising gelatin, acacia, glycerin and water; and the like.

The term beneficial agent as used herein means any composition, formulation, mixture, or compound that can be dispensed to produce a predetermined beneficial and useful result. The beneficial agents include algicides, antioxidants, air purifiers, biocides, catalysts, chemical reactants, cosmetics, drugs, disinfectants, fungicides, foods, fertility inhibitors, fertility promoters, food supplements, fermentation agents, germicides, insecticides, microorganism attenuators, nutrients, plant growth promoters, plant growth inhibitors, preservatives, surfactants, sterilization agents, sex steriIants, vitamins, and other compositions that benefit the environment, surrounds, habitats and animals. The agent can be insoluble to very soluble in the temperature sensitive material housed in the dispenser.

In the specification and the accompanying claims, the term drug includes any physiologically or pharmacologically active substance that produces a local or systemic effect in animals, including warm blooded mammals, humans and primates, avians, pisces, household, sport and farm animals, laboratory animals, and zoo animals. The term physiological as used herein denotes the administration of a drug to produce normal levels and functions. The term pharmacological denotes variations in response to amounts of drug administered to the host. *Stedman's Medical Dictionary,* 1966, published by Williams and Wilkins, Baltimore, MD. The active drug that can be delivered includes inorganic and organic drugs, drugs that are solid, drugs that are an oil, without limitations, those drugs that act on the nervous system, depressants, hypnotics, sedatives, psychic energizers, tranquilizers, anticonvulsants, muscle relaxants, antiparkinson agents, analgesics, anti-inflammatory, antimalarials, hormonal agents, contraceptives, sympathomimetics, diuretics, antiparasitics, neoplastics, hypoglycemics, ophthalmics, electrolytes, diagnostics, and cardiovascular drugs. The amount of agent present in the dispenser can be from 0.05 ng to 20 g or more. For medical applications, the dispenser can contain various amounts, for example 25 ng, 1 mg, 5 mg, 125 mg, 250 mg, 500 mg, 750 mg, 1.5 g, and the like. The dispenser can be used once, twice, or thrice daily; the dispenser can be used twice a week, and the like.

The semipermeable wall forming composition can be applied to the exterior surface of the capsule in laminar arrangement by molding, forming, air spraying, dipping or brushing with a semipermeable wall forming composition. Other and presently preferred techniques that can be used for applying the semipermeable wall are the air suspension procedure and the pan coating procedures. The air suspension procedure consists in suspending and tumbling the capsule arrangement in a current of air and a semipermeable wall forming composition until the wall surrounds and coats the capsule member. The procedure can be repeated with a different semipermeable wall forming composition to form a semipermeable laminated wall. The air suspension procedure is described in U.S. Pat. No. 2,799,241; *J. Am. Pharm. Assoc.,* Vol. 48, pages 451 to 459, 1979; and ibid, Vol. 49, pages 82 to 84, 1960. Other standard manufacturing procedures are described in *Modern Plastics Encyclopedia,* Vol. 46, pages 62 to 70, 1969; and in *Pharmaceutical Sciences,* by Remington, 14th Edition, pages 1626 to 1678, 1970, published by Mack Publishing Co., Easton, PA.

Exemplary solvents suitable for manufacturing the semipermeable wall include inert inorganic and organic solvents that do not adversely harm the materials, the capsule wall, the beneficial agent, the thermo-responsive composition, the expandable member, and the final dispenser. The solvents broadly include members selected from the group consisting of aqueous solvents, alcohols, ketones, esters, ethers, aliphatic hydrocarbons, halogenated solvents, cycloaliphatics, aromatics, heterocyclic solvents and mixtures thereof. Typical solvents include acetone, diacetone alcohol, methanol, ethanol, isopropyl alcohol, butyl alcohol, methyl acetate, ethyl acetate, isopropyl acetate, n-butyl acetate, methyl isobutyl ketone, methyl propyl ketone, n-hexane, n-heptane, ethylene glycol monoethyl ether, ethylene glycol monoethyl acetate, methylene dichloride, ethylene dichloride, propylene dichloride, carbon tetrachloride, nitroethane, nitropropane, tetrachloroethane, ethyl ether, isopropyl ether, cyclohexane, cyclooctane, benzene, toluene, naphtha, 1,4-dioxane, tetrahydrofuran, diglyme, water, and mixtures thereof such as acetone and water, acetone and methanol, acetone and ethyl alcohol, methylene dichloride and methanol, and ethylene dichloride and methanol. Generally, for the present purpose the semipermeable wall is applied at a temperature a few degrees less than the melting point of the thermo-responsive composition. Or, the thermoplastic composition can be loaded into the dispenser after applying the semipermeable wall.

The expression orifice or passageway as used herein comprises means and methods in the wall suitable for releasing a beneficial agent formulation from the dispenser. The orifice can be formed by mechanical or laser drilling, or by eroding an erodible element in the wall, such as a gelatin plug. The orifice can be a polymer inserted into the semipermeable wall, which polymer is a porous polymer and has at least one pore, or which polymer is a microporous polymer and has at least one micropore. A detailed description of orifices and the preferred maxium and minimum dimensions for an orifice are disclosed in U.S. Pat. Nos. 3,845,770 and 3,916,899.

DESCRIPTION OF EXAMPLES OF THE INVENTION

The following examples are merely illustrative of the present invention and they should not be construed as limiting the scope of the invention in any way, as these examples and other equivalents thereof will become more apparent to those skilled in the art in the light of the present disclosure, the drawings and the accompanying claims.

EXAMPLE 1

A dispenser is prepared as follows: First, the body section of a two piece capsule is positioned with its mouth in an upright position and the hemispherical end of the capsule charged with a layer of an expandable-swellable composition. The composition comprises 30% by weight of sodium chloride and 70% by weight of poly(ethylene oxide) having a molecular weight of 3,000,000. The expandable forming ingredients are blended in a commercial blender with heat for 20 minutes to yield a homogenous composition. The heated composition is charged into the hemispherical end of the capsule forming a layer that occupies about ¼ of the capsule. Next, the body section of the capsule is capped with the cap section of the capsule and a filling port is drilled through the cap for communicating with the lumen of the assembled capsule. Then, a heat sensitive drug formulation is passed through the filling port into the lumen of the capsule filling the lumen. Finally, a semipermeable wall is applied around the assembled capsule and an exit passageway drilled through the semipermeable wall communicating with the filling port for dispensing drug formulation from the dispenser.

EXAMPLE 2

A dispenser is prepared as follows: First, the body section of a two piece capsule is positioned with its opened mouth in an upright position and the curved hemispherical end of the capsule is filled with a 500 mg layer of Cyanamer ® polyacrylamide, a hydrogel of approximately 200,000 mol. wt. Next, the body section of the capsule is capped with the cap section of the capsule. Then, a semipermeable wall is formed around the assembled capsule. The semipermeable wall is formed by blending 85 g of cellulose acetate having an acetyl content of 39.8% with 200 ml of methylene chloride and 200 ml of methanol, and spray coating the assembled capsule in an air suspension machine until a 0.25 mm thick semipermeable wall surrounds the capsule. The capsule is dried, and a 1.0 mm passageway is laser drilled through the semipermeable wall and the capsule wall communicating with the lumen of the capsule. Next, a heat sensitive enteric mixture of 77% neutral fat having a melting point of 35°–37° C. and 19.5% paraffin having a melting point of 52° C., is heated and liquified, and 3.5% acetylsalicylic acid added thereto. Then, the heated mixture is cooled to about 40° C., injected through the passageway into the lumen of the capsule, and the dispenser cooled to room temperature.

EXAMPLE 3

A dispenser for delivering a beneficial agent to a warm-blooded animal is prepared a follows: A mold having a shape and a configuration corresponding to the mouth and internal diameter of the body portion of a capsule, is filled with an expandable forming composition comprising 30 parts of ethyleneglycol monomethacrylate containing 0.12 parts of ethyleneglycol dimethacrylate and 10 parts of a 0.13% aqueous solution of sodium disulfate in aqueous ethanol. The composition polymerizes at 30° C., and after 20 minutes following equilibrium to room temperature, the solid layer is removed from the mold. The solid expandable layer then is placed into the mouth of the capsule, thereby forming an internal drug compartment in the space between the curved hemispherical end of the capsule and the inner surface of the layer of the expandable polymer. Next, a filling-exit port is drilled through the hemispherical end connecting the exterior of the capsule with the interior compartment. The compartment can be filled with a heat-sensitive drug formulation at this time, or optionally it can be filled at a later time.

For example, the compartment can be filled with a molten composition comprising 2.5% phenobarbital, 20.5% glycergelatin and 77% of theobroma oil, a glyceride of stearic, palmitic and lauric acids, to form on cooling to room temperature the thermo-responsive composition in laminar position with the expandable lamina. Next, the body of the capsule is closed with the capsule cap by sliding the cap over the mouth of the capsule.

Then, a solution of cellulose acetate, 15 wt %, with an acetyl content of 39.8%, is prepared and the fully assembled capsule coated with a semipermeable wall by dipping it into the solution for 15 times, first for a 10 second dip, then for 1 minute per dip, with an intervening 5 minutes drying period. Following the dipping the dispeners are dried at room temperature of 72° F., about 22° C., for 10 days. This procedure applies about a 2 mm semipermeable wall. A passageway is laser drilled through the semipermeable wall connecting the exterior of the dispenser with the filling-exit port and with the thermo-responsive lamina.

EXAMPLE 4

Figure 10:
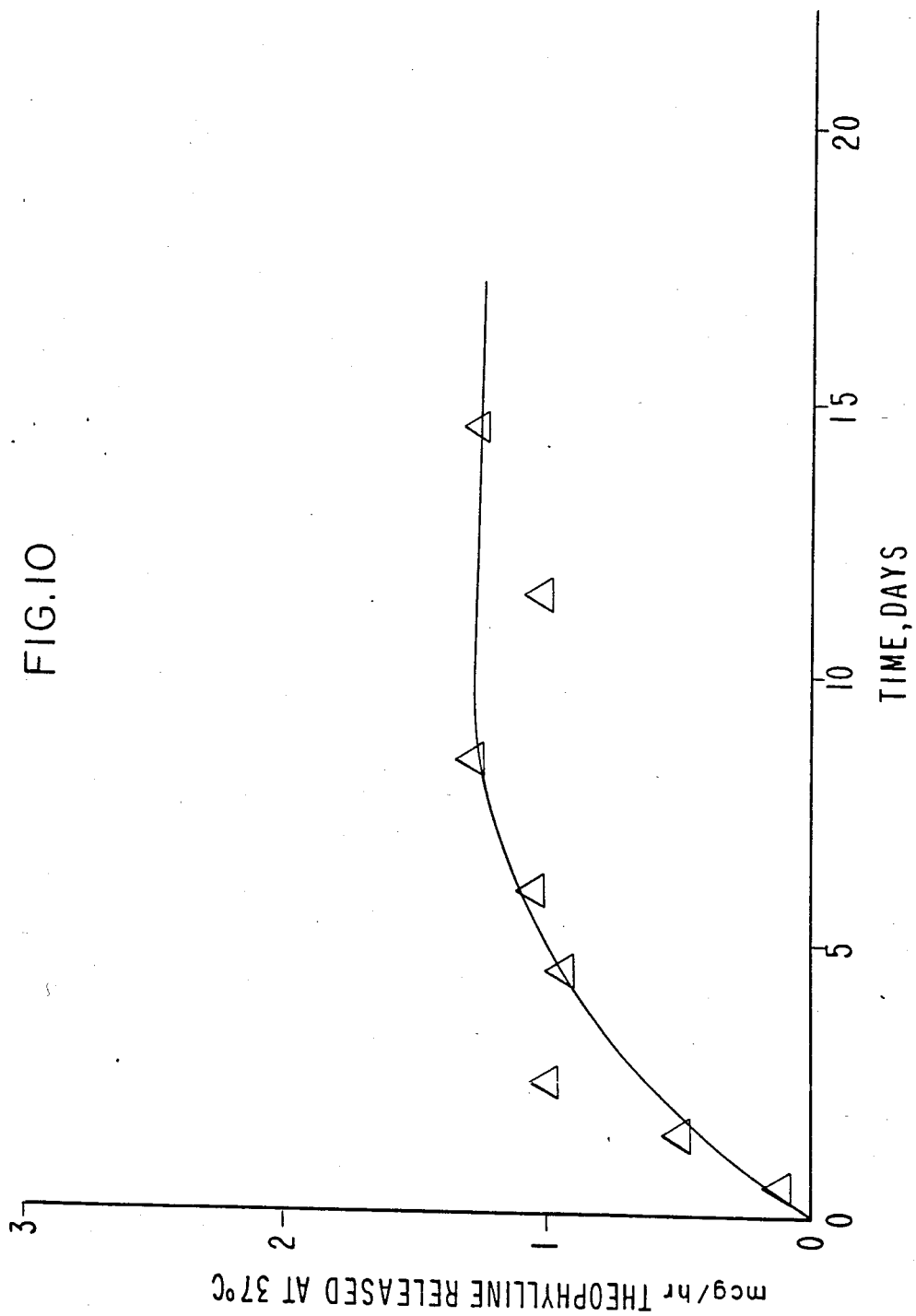

A dispenser for delivering a beneficial agent formulation is manufactured as follows: First, the hemispherical end of a gelatin capsule is filled with 3.25 g of a molten composition consisting essentially of 30% sodium chloride and 70% polyethylene oxide coagulant grade. Next, the cap of the capsule is dipped in water to a couple of millimeters and then the cap is slipped over the mouth end to cover the open body section of the capsule. The water causes the cap and body members of the capsule to bond in a firm relationship. Next, a 50 mil, 1.3 mm, exit port is drilled through the cap end of the assembled gelatin capsule. Then, 9.9 g of a thermo-sensitive drug formulation consisting of a 15% suspension of theophylline with 8% Cabosil ® anhydrous in polyethylene glycol 400 distearate is charged through the drug port into the drug chamber of the capsule at 50 ° C. forming a lamina in intimate contact with the expandable plug at the hemispherical end of the capsule. The thermo-responsitive drug formulation additionally contacts the inside gelatin capsule wall. Next, the assembled dosage form capsule is coated with a surrounding wall of cellulose acetate butyrate containing 10% polyethylene glycol 400. The semipermeable wall is applied in a pan Hi-coater. The solvent used for forming the wall consists essentially of methylene chloride methanol solvent consisting of 95 parts by weight to 5 parts by weight respectively. A 12 mil, 0.03 mm, thick wall of the cellulose acetate butyrate is applied to the exterior surface of the capsule. FIG. 10 shows the release rate in mgc per hour at 37° C.

An embodiment of the invention pertains to a method for administering a beneficial drug at a controlled rate to the vaginal passageway or to the ano-rectal passageway of a warmblooded animal, which method comprises the steps of: (A) admitting into the passageway a dispenser comprising: (1) an outer wall formed of a semipermeable polymeric composition permeable to the passage of fluid and substantially impermeable to the passage of drug; the wall surrounding (2) a capsule containing a layer of a beneficial drug formulation in the compartment comprising a dosage unit amount of drug for performing a therapeutic program in a heat-sensitive carrier that melts at body temperature and is a means for transporting the drug from the dispenser; (3) a layer of an expandable hydrogel in the capsule, said layer in contacting arrangement with the drug formulation heat sensitive composition; and, (4) an orifice through the outer wall and the capsule wall communicating with the drug formulation heat-sensitive composition; (B) imbibing fluid through the semipermeable wall at a rate determined by the permeability of the semipermeable wall and the osmotic pressure gradent across the semipermeable wall causing the layer of hydrogel to expand and swell; (C) melting the drug formulation to form a flowable formulation; and (D) delivering the beneficial drug formulation from the compartment by the layer continually expanding against the melted formulation causing the formulation to be dispensed in a therapeutically effective amount through the orifice at a controlled rate to the passageway to produce the desired medical effect over a prolonged period of 1 hour to months, preferrably 1 hour to 24 hours. Exemplary of a drug that can be dispensed using the dispenser is conjugated estrogen dispensed in a formulation comprising 0.875 mg of conjugated estrogens in a heat sensitive base.

Inasmuch as the foregoing specification comprises preferred embodiments of the invention, it is understood that variations and modifications may be made herein in accordance with the inventive principles disclosed, without departing from the scope of the invention.

We claim:

1. A dispenser for delivering a beneficial agent formulation to a biological environment of use, wherein the dispenser comprises:
   (a) a capsule member comprising a wall comprised of a gelatin composition that surrounds an internal compartment;
   (b) an opened mouth in the wall of the capsule;
   (c) means for absorbing fluid positioned in the mouth of the capsule, said means, when the dispenser is in operation in the biological environment, imbibing fluid, increasing in volume and expanding into the internal compartment;
   (d) a wall surrounding the exterior of the capsule member, said wall comprising in at least a part a semipermeable polymeric composition permeable to the passage of fluid and substantially impermeable to the passage of a beneficial agent; and,
   (e) a passageway in the wall and in the capsule distant and separate from the opened mouth and out of contact with the means for absorbing fluid for connecting the internal compartment with the exterior of the dispenser.

2. The dispenser for delivering a beneficial agent formulation according to claim 1, wherein the dispenser is filled and then admitted into the biological environment of use.

* * * * *